United States Patent [19]

Hillman

[11] 4,454,109
[45] Jun. 12, 1984

[54] METHOD OF TREATING PERIODONTOSIS

[75] Inventor: Jeffrey D. Hillman, Boston, Mass.

[73] Assignee: Forsyth Dental Infirmary for Children, Boston, Mass.

[21] Appl. No.: 357,167

[22] Filed: Mar. 11, 1982

Related U.S. Application Data

[63] Continuation-in-part of Ser. No. 235,130, Feb. 17, 1981, abandoned.

[51] Int. Cl.³ .................... A61K 7/16; A61K 7/20; A61K 33/40; A61K 39/09
[52] U.S. Cl. .................................... 424/50; 424/93
[58] Field of Search ......................... 424/93, 50

[56] References Cited

U.S. PATENT DOCUMENTS

| | | | |
|---|---|---|---|
| 3,931,398 | 1/1976 | Gaffar et al. | 424/50 |
| 3,993,747 | 11/1976 | Gaffar et al. | 424/50 |
| 4,133,875 | 1/1979 | Hillman | 424/93 |

Primary Examiner—Shep K. Rose
Attorney, Agent, or Firm—Richard P. Crowley

[57] ABSTRACT

A method of treating and preventing periodontosis caused by the presence of *Actinobacillus actinomycetemcomitans*, particularly juvenile periodontosis, which method comprises: contacting the oral cavity of the patient with an inhibitory amount of an effector strain of *Streptococcus sanguis*, *Strep. uberis* or *Actinomyces bovis*.

12 Claims, No Drawings

METHOD OF TREATING PERIODONTOSIS

REFERENCE TO PRIOR APPLICATION

This application is a continuation-in-part of application Ser. No. 235,130, filed Feb. 17, 1981 (now abandoned).

SUPPORT

The invention disclosed and claimed herein was supported in part by a grant from the National Institute of Dental Research (Grant DE-04529).

BACKGROUND OF THE INVENTION

Recent studies have implicated *Actinobacillus actinomycetemcomitans* as a possible etiologic agent of juvenile periodontitis (periodontosis). The organism has been recovered with greater frequency and in higher numbers from lesions of periodontosis than healthy sites in the same individuals or from lesions of gingivitis or periodontitis (Mandell and Socransky, 1980; Slots et al, 1980). Serum antibody titers to the organism are more frequently elevated in patients with periodontosis, when compared to healty individuals and individuals with other forms of periodontal disease (Ebersole et al, 1980a,b; Genco et al, 1980; Lai and Listgarten, 1980). Strains of *Actinobacillus actinomycetemcomitans* produce a toxin capable of lysing polymorphonuclear leukocytes (Baehni et al, 1979; Baehni et al, 1980). Antibodies to this toxin may be detected in periodontosis patients which are protective against the toxins lytic effect (McArthur et al, 1980). *Actinobacillus actinomycetemcomitans* has been shown to accelerate alveolar bone loss in gnotobiotic rats (Irving et al, 1975). *Actinobacillus actinomycetemcomitans* does not appear to be a numerically dominant member of the microbiota of individuals without adolescent destructive disease, but can attain proportions as high as 70% of the cultivable microbiota in sites of advanced destruction.

SUMMARY OF THE INVENTION

My invention relates to a method of treating or preventing periodontal disease and, in particular, preventing juvenile periodontosis caused by the establishment or overgrowth of the microorganism *Actinobacillus actinomycetemcomitans*.

It has been discovered that certain microorganisms resident in healthy periodontal sites, or sites with a different form of periodontal disease, prevent the establishment or overgrowth of *Actinobacillus actinomycetemcomitans*. It has been found that the growth of *Actinobacillus actinomycetemcomitans* is inhibited by the application of *Streptococcus sanguis, Strep. uberis* and *Actinomyces bovis* with *Streptococcus sanguis* being the preferred effector microorganism, particularly for the treatment and prevention of juvenile periodontosis characterized by a localized pattern of destruction and familial tendency. My invention provides a means and method for the bacterial interference with the growth of *Actinobacillus actinomycetemcomitans*.

The application of the effector strain of *Streptococcus sanguis, Strep. uberis* and *Actinomyces bovis* to the oral cavity of a patient, and particularly when placed in direct contact with affected tooth or teeth surfaces, prevents and cures periodontosis. The effector strain microorganism discovered may be introduced into the oral cavity in a number of forms and compositions, such as by the use of mouthwashes, mouthrinses, spray solutions and swabbing solutions or suspensions, by swabbing, spraying, rinsing, etc., techniques. In one method, a cell suspension of the selected effector strain, or combinations thereof, is swabbed directly onto and about the affected tooth or teeth surface, or the area to be protected, one or more times over a selected period of treatment time, depending on the patient and extent of the disease, until the periodontal disease is cured or prevented. A typical swabbing solution or suspension would include a culture medium or broth containing an effective or inhibitory amount of the effector strain therein. A swabbing solution would comprise, for example, a commercial Todd-Hewitt broth supplemented with a carbohydrate or sugar, such as a small amount of glucose of 0.1% to 2.0% by weight; for example, 0.50%, with about $10^9$ colonies/ml or more of the effector strain microorganism.

Effector microorganisms have been isolated and characterized and found to be the same as or similar to known microorganisms identified as *Strep. uberis, Streptococcus sanguis* and *Actinomyces bovis*. For example, strains used in this invention are identified as KJ2 (*Strep. uberis*) and KJ3 (*Streptococcus sanguis*) and have been isolated, characterized and discovered to be effective in preventing the establishment or growth of *Actinobacillus actinomycetemcomitans* and are the same as *Strep. uberis* strain ATCC 19436 and *Streptococcus sanguis* Type II strain ATCC 10557, respectively.

My invention will be described for the purpose of illustration only in connection with certain embodiments. However, it is recognized that various changes and modifications can be made, all within the scope of my invention.

DESCRIPTION OF THE EMBODIMENTS

Bacterial Strains and Media. Cultures of *Actinobacillus actinomycetemcomitans* strain Y4 were grown in mycoplasma broth (Baltimore Biologic Laboratories, Cockeysville, Md.), supplemented with 0.1% glucose, 5 ug/ml hemin and 1 mg/ml sodium bicarbonate as previously described. The medium was inoculated from 50% (v/v) glycerol stabs maintained at $-20°$ C. and incubated aerobically overnight at 37° C.

Plaque Sampling. Supra or subgingival plaque samples were obtained from healthy and periodontosis patients, using the methods of Newman and Socransky (1977). The samples were dispersed by sonication for 10 seconds with an MSE sonic oscillator and serial 10-fold diluted samples spread on trypticase soy agar (BBL) plates, supplemented with 5% sheep blood. The plates were incubated for 3 to 4 days at 37° C. in an atmosphere of 80% $N_2$, 10% $CO_2$ and 10% $H_2$.

Inhibitor Screening. A lawn of strain Y4 was prepared on chocolate agar medium by cross-streaking 0.2 ml of an overnight culture diluted 1:1000 with phosphate-buffered saline (pH 7). One hundred to five hundred random isolated colonies obtained from the plaque samples on blood agar plates were replica-stabbed, using sterile toothpicks, onto chocolate agar plates with and without a lawn of strain Y4. The plates were then incubated for 2 days at 37° C. in an atmosphere of 80% $N_2$, 10% $CO_2$ and 10% $H_2$. Interference was considered present, when direct visual examination revealed a zone of complete inhibition surrounding the stab. Results are expressed as the percentage of plaque isolates tested which inhibited the growth of strain Y4.

Results

Plaque samples obtained from seven subjects, who were free of clinically evident periodontal pathology, were analyzed for their content of inhibitory organisms to *Actinobacillus actinomycetemcomitans*. As seen in Table 1, it was found that all but one of the eleven sites samples harbored such organisms.

By contrast, fifteen of sixteen plaque samples, obtained from active disease sites of periodontosis patients, failed to demonstrate the presence of inhibitors. The samples were taken from a total of sixteen supra and subgingival sites representing six different patients. Five of these subjects demonstrated clinical manifestations of uncomplicated juvenile periodontosis. The sixth subject demonstrated a characteristic Papillon LeFevre syndrome. Interestingly, four of the five healty sites, which were samples from three of these patients, demonstrated the presence of inhibitory strains and in proportions comparable to plaque samples from nondiseased subjects.

Plaque samples from the four first molars of the mother and three siblings of one periodontosis subject were analyzed for their content of inhibitory organisms. As seen in Table 2, plaque from the mother, who has a history of destructive periodontal disease beginning in adolescence and currently presents with advanced generalized destructive disease, lacked inhibitory organisms in all of the four sites sampled. All of the siblings, aged 7, 9 and 11, lacked inhibitors in at least one of the four sites tested, and, in the case of one subject, all four of the sites were found to be affected.

TABLE 1

Percentage of Isolates Inhibitory to *Actinobacillus actinomycetemcomitans*

| Sites | Periodontosis Patients Diseased | Periodontosis Patients Healthy | Healthy Subjects Healthy |
|---|---|---|---|
| | 0 | | |
| | 0 | | |
| | 0 | | |
| | 0 | 0 | 0 |
| | 0 | 5.0 | 1.6 |
| | 0 | 8.4 | 2.8 |
| | 0 | 16.4 | 4.3 |
| | 0 | 44.0 | 5.3 |
| | 0 | | 5.8 |
| | 0 | | 7.0 |
| | 0 | | 9.0 |
| | 0 | | 13.0 |
| | 0 | | 15.8 |
| | 0 | | 29.0 |
| | 0 | | |
| | 32 | | |
| Median | 0 | 8.4 | 5.8 |
| 95% Confidence Interval to Median | 0—0 | 0–44* | 1.6–15.8 |

*93.75% confidence interval of the median, since only 5 samples studied.
Differences between groups significant at $p < 0.01$ using Kruskal-Wallis test.

TABLE 2

Percentage of Isolates Inhibitory to *Actinobacillus actinomycetemcomitans* in Plaque from Mother and Siblings of Periodontosis Patient

| Subject | Inhibitors (%) |
|---|---|
| Mother | 0 |
| | 0 |
| | 0 |
| | 0 |
| Sibling | 23 |
| | 1 |
| | 0 |
| | 5 |
| Sibling | 0 |
| | 0 |
| | 0 |
| | 0 |
| Sibling | 42 |
| | 9 |
| | 7 |
| | 0 |

1. Isolation of KJ2 and KJ3. Subgingival plaque was obtained from the first molar region of a clinically normal adult female. The sample was diluted in sterile phosphate-buffered saline (pH 7.0) and spread on blood agar plates, to give isolated colonies. Following three days incubation at 37° C. in an atmosphere of 80% $N_2$, 10% $H_2$ and 10% $CO_2$, single colonies which appeared were picked with sterile toothpicks and replica-stabbed into blood agar plates with and without a lawn of *Actinobacillus actinomycetemcomitans* strain Y4. After two days incubation at 37° C. in an atmosphere of 80% $N_2$, 10% $H_2$ and 10% $CO_2$, the stabs were examined for zones of inhibition of the Actinobacillus lawn. KJ2 and KJ3 were isolated from the replica of stabs, which produced clear zones of inhibition of the Actinobacillus lawn measuring ca. 3 mm.

2. Characterization of KJ2 and KJ3. Both strains produce small α hemolytic colony types on trypticase soy agar containing 5% sheep red blood cells. Both strains are gram-positive cocci, typically presented in pairs and chains. KJ2 has been identified as a representative of the class of bacteria called *Streptococcus uberis* on the basis of the following tests: gas liquid chromatography of culture liquors indicate lactic, formic and acetic acids to be the chief end-products of glucose fermentation. It can ferment the following compounds to produce acid: arabinose, cellobiose, glucose, glycerol, inulin, lactose, maltose, mannitol, melibiose, raffinose, salicin, sucrose, trehalose and xylose. It is negative in tests for esculin hydrolysis, nitrite and nitrate reduction, ammonia production from urea, and growth in the presence of 40% bile. The organism was found to produce ammonia from argenine and to degrade hippuric scid. It also produces hydrogen peroxide, when grown in an atmosphere of air plus 10% $CO_2$.

KJ3 has been identified as a representative of the class of bacteria called *Streptococcus sanguis* II on the basis of the following tests: gas liquid chromatography of culture liquors indicate lactic, formic and acetic acids to be the chief end-products of glucose fermentation. It can ferment the following compounds: glucose, lactose, maltose, mannitol, melibiose, raffinose, salicin, sucrose and trehalose. It cannot ferment cellobiose, glycerol, inulin, or xylose. It cannot hydrolyze esculin, reduce nitrite or nitrate, produce ammonia from argenine or urea, degrade hippuric acid, or grow in the presence of 40% bile. It does produce hydrogen peroxide, when grown in an atmosphere of air plus 10% $CO_2$.

3. Use of KJ2 and KJ3 in the prevention and cure of juvenile periodontosis. The potential usefulness of KJ2 and KJ3 as effector strains, in the prevention and/or treatment of juvenile periodontosis, relates to their ability to inhibit the growth of *Actinobacillus actinomycetemcomitans*, the etiologic agent of this disease. Three groups of five germ-free Sprague-Dawley rats were maintained in separate stainless-steel isolators. At 21 days of age, animals in isolator 1 were infected by swabbing their oral cavities with an overnight culture of KJ2. Animals in isolator 2 were similarly treated with a culture of KJ3. Animals in isolator 3 were sham-infected with sterile medium. Two weeks later, animals in all three isolators were challenged by swabbing the oral cavities with a culture of Y4 diluted to give ca. $10^4$ c.f.u./ml. At weekly intervals, plaque and saliva samples were obtained, and then the animals were reinfected, using a 10-fold higher concentration of Y4 than that used the previous week. It was found that animals in isolator 3 (sham-infected) became uniformly infected with Y4, when challenged with a concentration of cells equal to $10^6$ c.f.u./ml. By contrast, animals previously infected with KJ2 (isolator 1) or KJ3 (isolator 2) were not infected by Y4, even when challenged with concentrations of cells as high as $10^9$ c.f.u./ml. Thus, by preventing the colonization of the oral cavity by *Actinobacillus actinomycetemcomitans*, it is presumed that establishment of KJ2 and KJ3 in the mouths of individuals at risk could provide lifelong protection from juvenile periodontosis.

In a second experiment, two groups of two germ-free rats were monoinfected at 21 days of age with *Actinobacillus actinomycetemocmitans* strain Y4 by swabbing their oral cavity with an overnight culture. During the next four weeks, it was determined that Y4 had successfully colonized the oral cavities of these animals. One group of rats was then challenged with KJ2 or KJ3. At weekly intervals thereafter, the oral cavities of these animals were sampled, to determine the presence of Y4 and KJ2 and KJ3. It was found that animals challenged with KJ2 maintained their infection with Y4, although they did become colonized by KJ2. By contrast, animals challenged with KJ3 were free of Y4 infection and were heavily colonized by KJ3 after one week. These results indicate the potential usefulness of KJ3 as an agent for the treatment of active juvenile periodontosis.

The role of *Actinobacillus actinomycetemcomitans* in adolescent, destructive, periodontal diseases remains to be established indisputably. However, it appears that healthy individuals and individuals with other forms of periodontal disease harbor organisms, as discovered, in the gingival crevice area, which are inhibitory to *Actinobacillus actinomycetemcomitans* or other putative pathogens, making it difficult for the pathogen to establish or achieve sufficient numbers to initiate or maintain local pathology. Whether *Actinobacillus actinomycetemcomitans* is the pathogen in the affected adolescents or not, it seems clear that its presence in the lesion was not inhibited by associated microorganisms. It has been established that the absence of low numbers in individuals of *Actinobacillus actinomycetemcomitans*, without adolescent, destructive, periodontal disease, may be attributed at least in part to the presence of the discovered strains of antagonistic microorganisms. The mother and siblings of one periodontosis patient had one or more sites which lacked inhibitors. In the case of the siblings, no overt periodontal pathology was evident. The mechanism of inhibition by the discovered inhibitory organisms is not known. It does not appear to be acid formation, since carbohydrate in the medium was limited, and pure cultures of highly acidogenic organisms, such as *Streptococcus mutans*, were not inhibitory. The examples established that the microorganisms KJ2 and KJ3 prevented periodontosis (experiment 1), and KJ3 cured periodontosis (experiment 2), although other experiments have also shown that KJ2 also partially cures and that the *Actinomyces bovis* also is an effective, but not preferred, microorganism.

The invention is described with reference to the treatment of periodontosis; however, it is recognized that the method of the invention also may be employed usefully for the treatment of other diseases of the oral cavity, including other periodontal diseases, such as periodontosis.

The method of treatment and prevention does not involve an immunization technique, wherein killed cells are employed to generate antibodies, but rather relates to the employment of live strains of particular microorganisms, apparently to generate hydrogen peroxide and to inhibit the establishment and growth of *Actinobacillus actinomycetemcomitans* in the oral cavity, thereby inhibiting or preventing diseases related thereto. The microorganism strains ATCC 19436 and ATCC 10557 are introduced into the oral cavity in an effective amount, typically with an inert pharmaceutically acceptable carrier. The identification KJ2 and KJ3 has been employed for the purpose of internal identification; however, these strains are the same as and have all the characteristic properties of strains ATCC 19436 and ATCC 10557, respectively, and such ATCC strains may be used in the practice of the invention. Such microorganism strains have not been employed previously in the treatment and prevention of diseases of the oral cavity, particularly for periodontal disease.

LITERATURE CITED

1. Baehni, P., Tsai, C., McArthur, W. P., Hammond, B. F. and Taichman, N. S. (1979), VII. Detection of leukotoxic activity of a plaque derived gram negative organism. Infect. and Immun. 24: 233–243.
2. Baehni, P., Tsai, C., McArthur, W. P., Hammond, B. F., Socransky, S. S. and Taichman, N. S. (1980), Leukotoxicity of various *Actinobacilli actinomycetemcomitans*. J. Dent. Res. 59: (Special Issue A, Abstract 223).
3. Ebersole, J. L., Frey, D. E., Taubman, M. A., Smith, D. J. and Genco, R. J. (1980), Serum antibody response to *A. actinomycetemcomitans* (Y4) in periodontal diseases, J. Dent. Res. 59: (Special Issue A, Abstract 249).
4. Ebersole, J. L., Frey, D. E., Taubman, M. A., Smith, D. J., Genes, R. J. and Hammond, B. F. (1980), Antibody response to antigens from *A. actinomycetemcomitans* (Y4): Relationship to localized juvenile periodontitis (LJP). J. Dent. Res. 59: (Special Issue A, Abstract 255).
5. Genco, R. J., Taichman, N. A. and Sadowski, C. A. (1980), Precipitating antibodies to *Actinobacillus actinomycetemcomitans* in localized juvenile periodontitis. J. Dent. Res. 59: (Special Issue A, Abstract 246).
6. Irving, J. T., Newman, M. G., Socransky, S. S. and Heely, J. D. (1975), Histological changes in experimental periodontal disease in rats moninfected with a gram negative organism. Arch. Oral Biol. 20: 219–220.
7. Lai, C. H. and Listgarten, M. A. (1980), Circulating antibody titers to *Actinobacillus actinomycetemcomitans* in patients with periodontal disease. J. Dent. Res. 59: (Special Issue A, Abstract 975).

8. Mandell, R. L. and Socransky, S. S. (1980), A selective medium for *Actinobacillus actinomycetemcomitans*. J. Dent. Res. (Special Issue A, Abstract 972).

9. McArthur, W. P., Tsai, C. C., Baehni, P., Genco, R. J. and Taichman, N. (1980), Modulation of *Actinobacillus actinomycetemcomitans* (Y4) leukotoxicity by serum. J. Dent. Res. 59: (Special Issue A, Abstract 225).

10. Newman, M. G., Socransky, S. S. (1977), Predominant cultivable microbiota in periodontosis. J. Perio. Res. 12: 120–128.

11. Slots, J., Reynolds, H. S., Lobbins, P. N. and Genco R. J. (1980), *Actinobacillus actinomycetemcomitans*: Selective culturing and oral ecology in patients with localized juvenile periodontitis. J. Dent. Res. 59: (Special Issue A, Abstract 244).

What I claim is:

1. A method of treating periodontal disease caused by the etiological agent *Actinobacillus actinomycetemcomitans* in the oral cavity of a patient affected therewith, which method comprises:

introducing into the oral cavity an effective amount of a micro-organism hydrogen peroxide generating effector strain selected from the group consisting of *Streptococcus sanguis*, and Strep. uberis to inhibit the growth of *Actinobacillus actinomycetemcomitans*.

2. The method of claim 1 wherein the effective amount comprises about $10^9$ colonies/ml or more of the microorganism.

3. The method of claim 1 which includes introducing into the oral cavity of the patient a culture medium containing a small amount of glucose and the hydrogen peroxide generating effector strain of the microorganism.

4. The method of claim 1 which includes directly contacting the tooth or teeth area of a patient with a culture medium containing the effector strain microorganism.

5. The method of claim 4 which comprises swabbing the tooth or teeth area of a patient with the culture medium.

6. The method of claim 1 which includes contacting the oral cavity of a juvenile patient characterized by a localized pattern of periodontosis and familial tendency toward periodontosis.

7. The method of claim 1 wherein the hydrogen peroxide generating effector strain *Streptococcus sanguis* is strain ATCC 10557 and *Strep. uberis* is strain ATCC 19436.

8. A method of treating periodontosis caused by the etiological agent Actinobacillus actinomycetemcomitans in the oral cavity of a patient affected therewith, which method comprises:

(a) introducing into the oral cavity an effective amount of about $10^9$ colonies/ml or more of a microorganism hydrogen peroxide generating effector strain selected from the group consisting of *Streptococcus sanguis* II ATCC 10557 and *Strep. uberis* ATCC 19436; and (b) directly contacting the tooth or teeth area of a patient with a culture medium containing the hydrogen peroxide generating effector strain microorganism to inhibit the growth of Actinobacillus actinomycetemcomitans.

9. A method of inhibiting the bacterial growth of the microorganism *Actinobacillus actinomycetemcomitans*, which method comprises:

contacting the *Actinobacillus actinomycetemcomitans* with an effective inhibitory amount of a microorganism effector strain selected from the group consisting of *Streptococcus sanguis* and *Strep. uberis*.

10. The method of claim 9 wherein the effective amount comprises about $10^9$ colonies/ml or more of the microorganism.

11. The method of claim 9 which comprises employing a composition comprising a Todd-Hewitt broth from 0.1% to 2.0% by weight of a carbohydrate and about $10^9$ colonies/ml or more of the effector strain microorganism.

12. The method of claim 9 wherein the effector strain *Streptococcus sanguis* is strain ATCC 10557.

* * * * *